United States Patent [19]

McVicker et al.

[11] 4,154,751

[45] May 15, 1979

[54] PREPARATION AND USE OF SUPPORTED POTASSIUM (OR RUBIDIUM)-GROUP VIII-METAL CLUSTER CATALYSTS IN CO/$H_2$ FISCHER-TROPSCH SYNTHESIS REACTIONS

[75] Inventors: Gary B. McVicker, Westfield, N.J.; M. Albert Vannice, Boalsburg, Pa.

[73] Assignee: Exxon Research & Engineering Co., Florham Park, N.J.

[21] Appl. No.: 882,331

[22] Filed: Mar. 1, 1978

[51] Int. Cl.$^2$ ............................................. C07C 1/04
[52] U.S. Cl. .................... 260/449.6 R; 260/449 R; 260/449 M; 260/449.6 M; 252/443; 252/447; 252/466 PT; 252/461 J; 252/474
[58] Field of Search ..................... 260/449 R, 449 M

[56] References Cited

U.S. PATENT DOCUMENTS

| | | | |
|---|---|---|---|
| 2,533,071 | 12/1950 | Vesterdal et al. | 260/449.6 |
| 2,567,295 | 9/1951 | Milligan et al. | 260/449.1 |
| 3,833,634 | 9/1974 | Pruett et al. | 260/449 R |
| 3,952,039 | 11/1976 | Walker et al. | 260/449 R |
| 3,957,857 | 5/1976 | Pruett et al. | 260/449 R |

Primary Examiner—Howard T. Mars

Attorney, Agent, or Firm—Joseph J. Allocca

[57] ABSTRACT

This invention relates to unique supported potassium (or rubidium)-Group VIII-metal cluster catalysts which are useful in CO/$H_2$ reactions (Fischer-Tropsch synthesis reactions). The novel catalysts of the instant invention are prepared by depositing well characterized potassium (or rubidium)-Group VIII-metal carbonyl cluster complexes onto high surface area supports. Following a subsequent reduction, the precursor bimetallic cluster complexes are decomposed on the support surface forming a potassium (or rubidium) promoted Group VIII-metal cluster catalyst in which the potassium (or rubidium) and Group VIII metals are intimately associated. These unique, highly promoted cluster catalysts have been found to demonstrate high Group VIII-metal dispersions and enhanced Fischer-Tropsch activities and selectivities for producing olefinic and paraffinic hydrocarbons. In addition methane formation is dramatically reduced over the supported bimetallic cluster catalysts of the instant invention when compared to conventionally prepared supported potassium (or rubidium) promoted Group VIII-metal catalysts.

15 Claims, No Drawings

PREPARATION AND USE OF SUPPORTED POTASSIUM (OR RUBIDIUM)-GROUP VIII-METAL CLUSTER CATALYSTS IN CO/H$_2$ FISCHER-TROPSCH SYNTHESIS REACTIONS

BACKGROUND OF THE INVENTION

Potassium has been known for quite a long time to enhance the formation of longer chain and olefinic hydrocarbons over bulk Group VIII-metal catalysts, especially iron, which are used in the Fischer-Tropsch synthesis reaction. Potassium, however, facilitates the sintering of the Group VIII-metal surfaces. To minimize sintering, oxide supports such as SiO$_2$ and Al$_2$O$_3$ have been used to stabilize the Group VIII-metal surface areas. The use of high surface area supports tends, however, to physically separate the potassium and Group VIII-metals which diminishes the promotional effect of potassium (or rubidium). Thus, in the preparation of Group VIII-metal Fischer-Tropsch catalysts, a careful balance between promotional and stabilization additives must be achieved to maximize activity and selectivity patterns.

Bulk Group VIII-metal catalysts are very poorly dispersed and thus possess very low surface/volume ratios. Supported Group VIII-metal catalysts, however, contain much smaller crystallite sizes and correspondingly larger surface/volume ratios. Supports also function to stabilize small Group VIII-metal crystallites against thermal sintering. The heretofore disadvantage of well-dispersed supported Group VIII-metal catalysts is the extreme difficulty of effectively promoting such catalysts with potassium (or rubidium). The difficulty arises since the added potassium (or rubidium) promoter has a tendency to preferentially affix itself to the high surface area support rather than to the small Group VIII-metal crystallites. This of course reduces greatly the promotional effect of potassium (or rubidium).

Typically, prior art catalysts are prepared by first impregnating a support with a Group VIII-metal salt. Following reduction of the Group VIII-metal salt a potassium (or rubidium salt) is then deposited. Conversely, a support may be first impregnated with a potassium salt (or rubidium salt) and then subsequently impregnated with a Group VIII-metal salt, and then reduced. Alternately, a potassium salt (or rubidium salt) and a Group VIII-metal salt may be co-impregnated onto a support and then reduced so as to produce a supported bimetallic K (or Rb)/Group VIII-metal catalyst system.

THE INSTANT INVENTION

The instant invention comprises a supported potassium (or rubidium)-Group VIII-metal catalyst characterized by the existence of discrete potassium-Group VIII-metal clusters on the support surface. The promoted bimetallic cluster catalysts of the instant invention are prepared by impregnating a high surface area support with a soluble potassium (or rubidium)-Group VIII-metal carbonyl cluster complex and then reducing the complex to the metallic state.

The use of preformed potassium (or rubidium)-Group VIII-metal carbonyl cluster complexes as precursors for the preparation of supported bimetallic Fischer-Tropsch catalysts is a novel synthetic technique. First of all, this technique provides a route for preparing well dispersed Group VIII-metal phases. Second, the stoichiometry of the potassium (or rubidium)-Group VIII-metal carbonyl cluster complexes can be characterized and varied thereby allowing a direct control over the number and type of metal atoms per cluster. Third, the presence of Group IA and IB metals, especially K, Rb and Cu promote Group VIII-metals for the Fischer-Tropsch (CO/H$_2$) synthesis reaction. Since well-defined potassium (and rubidium)-Group VIII-metal carbonyl complexes can be prepared with varying K (or Rb)/Group VIII-metal ratios, a wide range of supported catalyst stoichiometries are possible using such cluster complexes as precursors. Finally, since potassium (or rubidium) and the Group VIII-metals are in intimate contact in the precursor cluster complexes, the deposition and subsequent reduction of such complexes on a support surface maximizes the promotional effect of potassium (or rubidium) on the Group VIII-metals. The preparative technique herein disclosed finds general application in the promotion of supported Group VIII-metal catalysts with potassium (or rubidium), for example, promoted supported ruthenium catalysts, promoted supported cobalt catalysts, promoted supported rhodium catalysts, promoted supported iridium catalysts, promoted supported nickel catalysts, promoted supported palladium catalysts and promoted supported platinum catalysts. The promoters are preferably potassium or rubidium. High surface area supports may be selected from refractory inorganic oxides or carbon, typically alumina, silica, titania, zirconia, hafnia, tantala, niobia, vanadia, tungsten oxide, silica-alumina, magnesia, chromia, molybdenia, etc., preferably alumina, silica-alumina, titania, magnesia, hafnia, zirconia, most preferably alumina, silica-alumina, magnesia and titania. The precursor potassium (or rubidium)-Group VIII-metal carbonyl cluster complexes may be deposited on the supports from solution, the solution being either aqueous or nonaqueous depending upon the solubility and stability of the complexes, preferably the complexes are deposited from nonaqueous solutions.

| List of Precursor Bimetallic Cluster Complexes | |
|---|---|
| K$_2$Fe(CO)$_4$ | Rb$_2$Fe(CO)$_4$ |
| KFe(CO)$_2$C$_5$H$_5$ | RbFe(CO)$_2$C$_5$H$_5$ |
| KHFe(CO)$_4$ | RbHFe(CO)$_4$ |
| K$_2$Fe$_2$(CO)$_8$ | RbFe$_2$(CO)$_8$ |
| K$_2$Fe$_3$(CO)$_{11}$ | Rb$_2$Fe$_3$(CO)$_{11}$ |
| KFe(CO)$_3$NO | RbFe(CO)$_3$NO |
| K$_2$Ru(CO)$_4$ | Rb$_2$Ru(CO)$_4$ |
| KRu(CO)$_2$C$_5$H$_5$ | RbRu(CO)$_2$C$_5$H$_5$ |
| K$_2$Ru$_3$(CO)$_{12}$ | RbRu$_3$(CO)$_{12}$ |
| KHRu(CO)$_4$ | RbHRu(CO)$_4$ |
| K$_2$Ru$_2$(CO)$_8$ | Rb$_2$Ru$_2$(CO)$_8$ |
| KCo(CO)$_4$ | RbCo(CO)$_4$ |
| K$_2$Co$_6$(CO)$_{15}$ | Rb$_2$Co$_6$(CO)$_{15}$ |
| K$_4$Co$_6$(CO)$_{14}$ | Rb$_4$Co$_6$(CO)$_{14}$ |
| KHIr$_4$(CO)$_{11}$ | RbIr(CO)$_4$ |
| K$_2$Ir$_6$(CO)$_{15}$ | Rb$_2$Ir$_6$(CO)$_{15}$ |
| K$_2$Ir$_8$(CO)$_{20}$ | RbIr$_8$(CO)$_{20}$ |
| KRh(CO)$_4$ | RbRn(CO)$_4$ |
| K$_2$RH$_6$(CO)$_{15}$ | Rb$_2$Rh$_6$(CO)$_{15}$ |
| K$_3$Rh$_7$(CO)$_{16}$ | Rb$_3$Rh$_7$(CO)$_{16}$ |
| KNi$_2$(CO)$_6$ | RbNi$_2$(CO)$_6$ |
| KNi(CO)C$_5$H$_5$ | RbNi(CO)C$_5$H$_5$ |
| K$_2$Pt$_3$(CO)$_6$ | Rb$_2$Pt$_3$(CO)$_6$ |
| K$_2$Pt$_6$(CO)$_{12}$ | Rb$_2$Pt$_6$(CO)$_{12}$ |
| K$_2$Pt$_6$(CO)$_{18}$ | Rb$_2$Pt$_9$(CO)$_{18}$ |
| K$_2$Pt$_{12}$(CO)$_{24}$ | Rb$_2$Pt$_{12}$(CO)$_{24}$ |
| K$_2$Pt$_{15}$(CO)$_{30}$ | Rb$_2$Pt$_{15}$(CO)$_{30}$ |

The above is only a partial list and should only be considered representative and not exclusive.

The supported potassium (or rubidium)-Group VIII-metal carbonyl complexes are dried in the absence of oxygen and then reduced at elevated temperatures, the elevated reduction temperatures ranging from 200° to 800° C., preferably 350° to 600° C., most preferably 400° to 500° C. The reducing atmosphere is preferably a hydrogen-containing atmosphere. The reduction is conducted for a sufficiently long time to effect the essentially complete reduction of the supported potassium (or rubidium)-Group VIII-metal carbonyl cluster complexes to a discrete potassium (or rubidium)-Group VIII bimetallic cluster of metals on the support surface. Such bimetallic cluster catalyts typically contain 1 to 50% by weight Group VIII metal concentrations. Within the above weight % range, the Group VIII metal/potassium (or rubidium) mole ratio may vary between 0.33 and 30, preferably 0.33–20.

The instant invention is also directed to a method for the preparation of higher molecular weight hydrocarbons, both paraffinic and olefinic, which comprises passing a $CO/H_2$ mixture over the catalyst system described above at typical Fischer-Tropsch conditions. More particularly, the typical Fischer-Tropsch conditions comprise using CO and $H_2$ at a $H_2/CO$ ratio of from 0.1–10, preferably 0.5–4, most preferably 1–3, this gas mixture being passed over and contacted with a catalyst at a space velocity of from 100 $hr^{-1}$ to 50,000 $hr^{-1}$, for a time sufficient to effect the generation of the desired higher molecular weight hydrocarbons, the contacting of the $CO-H_2$ gas mixture with the catalyst being effected at a temperature of from 100° to 500° C., preferably 150°–400° C., most preferably 150°–300° C., at a pressure of from 100 to $10^5$ kPa, preferably 100 to 3000 kPa, most preferably 100–2000 kPa.

PREPARATION OF CATALYSTS

Air sensitive reactions and catalyst preparations using air sensitive complexes were carried out in a "dry box" employing a nitrogen atmosphere. Solvents were dried and degassed by standard techniques.
(A) 5.5% K, 3.9% Fe/$Al_2O_3$ The precursor complex, $K_2Fe(CO)_4 \bullet 2C_4H_8O$ was prepared by reducing $Fe_3(CO)_{12}$ with potassium metal chips in dry THF solution. The solid off-white $K_2Fe(CO)_4 \bullet 2C_4H_8O$ complex was collected by vacuum filtration and washed with n-heptane and finally vacuum ($10^{-4}$ mm) dried. 1.51 gm of $K_2Fe(CO)_4 \bullet 2C_4H_8O$ was dissolved in 6.0 ml of dry methanol. This dark yellow solution was used to impregnate 9.8 gm of dry n-$Al_2O_3$ (dried at 350° C., 4.0 hours at $10^{-4}$ mm). The alcohol solvent was removed with reduced pressure at room temperature. A second impregnation was carried out using a solution containing approximately 0.75 gm of $K_2Fe(CO)_4 \bullet 2C_4H_8O$ dissolved in 5.0 ml of methanol. The alcohol solvent was removed with reduced pressure ($10^{-4}$ mm) at room temperature. The catalyst was reduced at 500° C. for 2.0 hours under 20% $H_2$/He flowing at 500 cc/min. The reduced catalyst was found to contain 5.5% K, 3.9% Fe (K/Fe=2.0). The unreduced catalyst is extremely air-sensitive and undergoes a rapid exothermic decomposition.
(B) 2.2% K, 3.2% Fe/$Al_2O_3$ The precursor complex, K Fe(CO)$_2$(C$_5$H$_5$), was prepared by reducing a 100 ml THF solution of 3.17 gm of [Fe(CO)$_2$(C$_5$H$_5$)]$_2$ with 1.0 gm of potassium metal chips. The crude reaction mixture was filtered. The clear yellow filtrate was adjusted to 100 ml by addition of THF. 15 ml of this stock solution was used to impregnate 20 gm of dry n-$Al_2O_3$ (dried at 350° C., 4.0 hours $10^{-4}$ mm). The solvent was removed with reduced pressure at room temperature. The imregnation-vacuum drying procedure was repeated seven times. The vacuum dried catalyst was reduced at 500° C. for 2.0 hours under 20% $H_2$/He flowing at 500 cc/min. The reduced catalyst was found to contain 2.2% K, 3.2% Fe (K/Fe=1.0). The unreduced catalyst is extremely air-sensitive and undergoes a rapid exothermic decomposition.
(C) 6.7% K, 4.7% Fe/$SiO_2$ 1.51 gm of $K_2Fe(CO)_4 \bullet 2C_4H_8O$ was dissolved in 11.0 ml of dry methanol. The resulting dark-yellow solution was used to impregnate 5.0 gm of $SiO_2$ which was previously dried for 16 hours at 550° C. under flowing dry air. The solvent was removed with reduced pressure at room temperature. The vacuum dried catalyst was reduced at 500° C. for 2.0 hours under 20% $H_2$/He flowing at 500 cc/min. The reduced catalyst was found to contain 6.7% K, 4.7% Fe (K/Fe=2.0). The unreduced catalyst is extremely air sensitive and undergoes a rapid exothermic decomposition.
(D) 4.1% Cu, 3.7% Fe/$SiO_2$ The precursor complex, [(PMPT) CuFe(CO)$_4$]$_x$ (where PMDT=pentamethyldiethylenetriamine), was prepared by allowing 3.50 gm of $Na_2Fe(CO)_4 \bullet 2$ dioxane to react with 2.76 gm of [(PMDT) Cu Cl$_2$]$_x$ in 25 ml methanol solution. The reaction is monitored by watching the solution change from dark blue to light yellow. The crude solution was filtered to remove NaCl produced during the reaction. The filtrate was adjusted to 20 ml by the use of reduced pressure. The clear yellow filtrate was used to impregnate 10 gm of dry $SiO_2$ (dried at 550° C. under flowing air for 16 hours). The catalyst was dried with reduced pressure ($10^{-4}$ mm). The reduced catalyst was found to contain 3.7% Fe, 4.1% Cu $$\left( \frac{Cu}{Fe} = 1.0 \right).$$

The dry catalyst is extremely air sensitive.
(E) 0.45% K, 1.3% Ru/$Al_2O_3$

The precursor complex, $K_2[Ru_3(CO)_{12}]$, was prepared by reducing 0.843 gm of $Ru_3(CO)_{12}$ with 30 gm of a 1% K amalgam in 30 ml of dry THF under 50 psig CO pressure. The crude reaction mixture was filtered. The dark red filtrate was concentrated to 16 ml with reduced pressure at room temperature. The concentrate was used to impregnate 20 gm of dry n-$Al_2O_3$ (dried at 470° C. under flowing air for 72 hours). The THF solvent was removed with reduced pressure ($10^{-4}$ mm) at room temperature for 3.0 hours. The unreduced catalyst is extremely air sensitive. The reduced catalyst was found to contain 1.3% Ru, 0.45% K (K/Ru=0.9).
(F) 0.3% K, 1.4% Ir/$Al_2O_3$ The precursor complex, K Ir(CO)$_4$, was prepared by allowing 0.575 gm of $Ir_4(CO)_{12}$ to react with 30 gm of a 1% K amalgam in 30 ml of THF under 50 psig CO pressure. The crude reaction mixture was filtered. The cherry red filtrate was concentrated to 15 ml with reduced pressure. The concentrate was used to impregnate 20 gm of dry n-$Al_2O_3$ (dried at 470° C. for 72 hours under flowing air). The solvent was removed with reduced pressure ($10^{-4}$ mm) at room temperature for 3.0 hours. The unreduced catalyst is extremely air sensitive. The reduced catalyst was found to contain 1.4% Ir, 0.3% K (K/Ir=1.0).
(G) 5.5% K/3.9% Fe/$Al_2O_3$ (Conventional catalyst)

A 6.0 ml solution containing 2.8 gm $Fe(NO_3)_3 \cdot 9H_2O$ and 1.4 gm $KNO_3$ dissolved in distilled water was used to impregnate 9.1 gm of dry $n-Al_2O_3$ (dried at 130° C. for 16 hours under air). The impregnate was dried at 120°–130° C. for 72 hours under dry air. The dry catalyst was reduced under $H_2$ and contained 3.9% Fe, 5.5% K (K/Fe=2.0).

(H) 7.5% Rb, 4.9% $Fe/Al_2O_3$

The precursor complex, $RbFe(CO)_2C_5H_5$, was prepared by reducing a 100 ml THF solution of 3.54 gm of $(Fe(CO)_2C_5H_5)_2$ with 3.0 gm of fresh rubidium cuttings. The crude reaction mixture was filtered and the clear yellow filtrate was adjusted to 100 ml by addition of THF. 15 ml of this stock solution was used to impregnate 20 gm of dry $n-Al_2O_3$ (dried at 450° C., 4.0 hr $10^{-4}$ mm). The THF solvent was removed under reduced pressure at room temperature. The impregnation-vacuum drying procedure was repeated seven times. The vacuum dried catalyst was reduced at 400° C. for 2.0 hours under 20% $H_2$/He flowing at 500 cc/min. The reduced catalyst contained 7.5% Rb, 4.9% Fe (Rb/Fe=2.0). The unreduced catalyst is very air sensitive.

Prior to reduction, dry supported potassium (rubidium)-Group VIII-metal carbonyl cluster complexes were subjected to infrared measurements. Spectra in the carbonyl region were recorded on Nujol mull samples sandwiched between KBr salt plates. Infrared samples were prepared in the absence of air and moisture. The results of such infrared measurements are illustrated by the following examples. The mull infrared spectrum of a dry nonreduced sample of catalyst (B), 2.2% K, 3.2% $Fe/Al_2O_3$, exhibited a pair of strong carbonyl bonds at 1842 and 1753 $cm^{-1}$. The positions of these bonds are very close to those displayed by $KFe(CO)_2C_5H_5$ in THF solution (1864 and 1768 $cm^{-1}$). These observations clearly indicate that the bimetallic $KFe(CO)_2C_5H_5$ cluster complex remains intact on the dehydrated $Al_2O_3$ surface. Upon air exposure the supported $KFe(CO)_2C_5H_5$ cluster complex rapidly decomposes as noted by the loss in carbonyl band intensity. When subjected to hydrogen reduction the organic portion of the intact bimetallic cluster complex is destroyed, leaving behind reduced potassium and iron surface phases which are in close proximity and thus the promotional effect of potassium upon iron is maximized. To further illustrate the above, a mull infrared spectrum of a dry, nonreduced sample of catalyst (F), 0.3% K, 1.4% $Ir/Al_2O_3$, exhibited a strong carbonyl band at 1892 $cm^{-1}$ and a shoulder at 1868 $cm^{-1}$. The position and relative intensity of these bands are very similar to those exhibited by the precursor, $KIr(CO)_4$, complex in THF solution (1896s, 1863sh $cm^{-1}$). Thus, the $KIr(CO)_4$ precursor cluster complex remains intact on the dry $Al_2O_3$ surface. Upon exposure to air the 1892 and 1868 $cm^{-1}$ carbonyl bonds of the supported cluster complex are completely lost. Upon reduction of the intact bimetallic cluster complex the organic portion is destroyed leaving behind reduced potassium and iridium surface species which are in intimate contact and thus the promotional effect of potassium or iridium is maximized.

Potassium (or rubidium) promoted Group VIII-metal catalysts of the instant invention prepared by the deposition and subsequent reduction of preformed potassium (or rubidium)-Group VIII-metal carbonyl cluster complexes are characterized by high Group VIII-metal surface areas. The chemisorption of carbon monoxide was used to determine the Group VIII-metal surface areas of hydrogen-reduced catalyst samples. Surface areas were determined on both fresh catalysts and samples recovered from Fischer-Tropsch experiments. Carbon monoxide uptakes on $K/Al_2O_3$ samples were negligible and thus did not interfere with the determination of the Group VIII-metal surface areas. A fresh 5.5% K, 3.9% $Fe/Al_2O_3$ cluster catalyst (catalyst A) prepared by the method of the instant invention was found to adsorb 103 $\mu$mole of carbon monoxide per gm of catalyst (see Table I). This uptake corresponds to a CO/Fe ratio of 0.15. A sample of the same catalyst recovered from a Fischer-Tropsch experiment exhibited a CO/Fe value of 0.063. A used 5.5% K, 3.9% $Fe/Al_2O_3$ conventionally prepared catalyst (catalyst G) when subjected to the same Fischer-Tropsch condition as the cluster catalyst above exhibited a CO/Fe ratio of 0.037. These results show that a supported bimetallic K/Fe cluster catalyst maintains a much higher available Fe surface area than a conventionally prepared K/Fe bimetallic catalyst. Used samples of both K/Ru and K/Ir cluster catalysts exhibit large carbon monoxide uptakes indicating that the Group VIII-metals are well dispersed and stable toward the Fischer-Tropsch synthesis reactants. Carbon monoxide uptakes of reduced, supported potassium (or rubidium)-Group VIII metal cluster catalysts are generally higher on $Al_2O_3$ than on $SiO_2$ supports (compare catalysts (A) and (C)).

Bimetallic, supported cluster catalysts of the instant invention prepared by the above-cited techniques are useful in Fischer-Tropsch synthesis reactions. These novel catalysts are highly beneficial in that they demonstrate an enhanced selectivity for the production of olefins and exhibit a markedly lower methane make than conventional unpromoted and promoted Group VIII-metal Fischer-Tropsch catalysts.

Comparative Fischer-Tropsch synthesis experiments were carried out in a glass reactor system employing 0.3–0.5 gm of catalyst and a $H_2/CO=3$ synthesis gas mixture at 103 kPa (1.0 atm) total pressure. A gas chromatograph employing subambient temperature programming was used for product analysis. Low conversions (0.1–10%) were maintained to assure operation of a differential reactor and thereby eliminate effects due to heat and mass transfer, product inhibition and secondary reactions. Catalysts were subjected to a standard pretreatment which consisted of: a 0.5 hr. reduction at 120° C., heating to 260° C. and reducing for 0.5 hr. followed by heating to 450° C. where the sample was further reduced for 1.0 hr. Hydrogen flowing at 30–50 cc/minute was employed as the reducing agent. Catalysts were then cooled to the Fischer-Tropsch reaction temperature under hydrogen. The detailed product analyses of several bulk and supported iron catalysts are presented in Table II.

The most important aspects here are the low methane make and high olefin content of the higher molecular weight hydrocarbons produced over the $Al_2O_3$-supported cluster catalyst (catalyst A) of the instant invention. The product distribution and activity pattern displayed by this catalyst are clearly different and superior to the activity and product distribution shown by a conventionally prepared $Al_2O_3$-supported bimetallic K/Fe catalyst (catalyst G) of the same metal content and also to a conventionally prepared 10% $Fe/Al_2O_3$ catalyst. The product distribution and activity characteristics of the $Al_2O_3$-supported K/Fe cluster catalyst (catalyst A) are also superior to those displayed by bulk iron and by potassium-promoted bulk iron catalysts shown as the last two items in Table II.

The Fischer-Tropsch product distribution and activity (CO conversion) patterns of several representatives supported bimetallic cluster catalysts prepared by the methods of the instant invention are summarized in Table III. A comparison of catalyst [A] and [B] indicates that as the Group VIII—metal/K mole ratio of the precursor complex decreases from 2:1 to 1:1, catalyst activity increases while the quantity of olefinic and higher molecular weight products is lowered. A comparison of catalyst [A] and [C] in which the same precursor complex, namely, $K_2Fe(CO)_42C_4H_8O$, was used shows a marked decrease in activity occurs upon going from $Al_2O_3$ to a $SiO_2$ support. The activity and selectivity pattern demonstrated by a Cu-promoted $SiO_2$—supported cluster catalyst (catalyst D) appears to be similar to that exhibited by Catalyst B. The activity of a supported K/Ru cluster catalyst (catalyst E) was found to be considerably higher than a supported K/Ir cluster catalyst (catalyst F).

TABLE I

Carbon Monoxide Adsorption on Supported Bimetallic Catalysts at 25° C.

| Catalyst[a] | | CO Uptake (μmole/gm) | | CO/M[b] | |
|---|---|---|---|---|---|
| | | Fresh | Used | Fresh | Used |
| [A] | 5.5% K, 3.9% Fe/Al₂O₃ (cluster catalyst) | 103 | 44.3 | 0.15 | 0.063 |
| [G] | 5.5% K, 3.9% Fe/Al₂O₃ (conventional catalyst) | — | 25.6 | — | 0.037 |
| [E] | 0.45% K, 1.3% Ru/Al₂O₃ (cluster catalyst) | — | 66.3 | — | 0.51 |
| [F] | 0.3% K, 1.4% Ir/Al₂O₃ (cluster catalyst) | — | 43.0 | — | 0.59 |
| [C] | 6.7% K, 4.7% Fe/SiO₂ (cluster catalyst) | 23.2 | — | 0.029 | — |

[a] Catalysts were reduced under H₂ at 450° C. for 1.0 hr. prior to CO adsorption measurement. Samples were not exposed to O₂ before reduction.
[b] M is the Group VIII metal.

TABLE II

Comparison of the Fischer-Tropsch Catalytic Behavior of Bulk and Supported Iron Catalysts[a]

| Catalyst | T°C. | Product Wt. % | | | | | | | | | Activity μmole CO min. g Fe |
|---|---|---|---|---|---|---|---|---|---|---|---|
| | | C₁ | C₂= | C₂ | C₃= | C₃ | C₄= | C₄ | C₅ | C₆+ | |
| [A] 5.5% K, 3.9% Fe/Al₂O₃ (cluster catalyst) | 264 | 9 | 15 | 2 | 19 | tr | 16 | 5 | 20 | 15 | 150 |
| | 271 | 9.7 | 14 | 2 | 26 | tr | 20 | 4 | 13 | 11 | 227 |
| [G] 5.5% K, 3.9% Fe/Al₂O₃ (conventional catalyst) | 268 | 44 | 56 | 0 | 0 | 0 | 0 | 0 | 0 | 0 | 4.5 |
| 10% Fe/Al₂O₃ (conventional) | 264 | 50 | 2 | 23 | 1 | 10 | tr | 10 | 4 | 0 | 204 |
| Bulk Fe metal | 264 | 24 | 5 | 31 | 7 | 8 | tr | 17 | A 7 | 2 | 12 |
| Bulk K/Fe | 269 | 13 | 22 | 2 | 22 | tr | 24 | | 12 | 5 | 13 |

[a] H₂/CO=3.0, 103 kPA total pressure.

TABLE III

Fischer-Tropsch Product Distributions for Supported Bimetallic Cluster Catalysts[a]

| Catalyst | T°C. | Product Mole % | | | | | | | | | % CO Conversion |
|---|---|---|---|---|---|---|---|---|---|---|---|
| | | C₁ | C₂= | C₂ | C₃= | C₃ | C₄= | C₄ | C₅ | C₆+ | |
| [A] 5.5% K, 3.9% Fe/Al₂O₃ | 284 | 25 | 20 | 3 | 24 | | 11 | 2 | 6 | 9 | 5.4 |
| [B] 2.2% K, 3.2% Fe/Al₂O₃ | 263 | 52 | 4 | 9 | 17 | | 10 | | 6 | 2 | 7.1 |
| [C] 6.7% K, 4.7% Fe/SiO₂ | 279 | 754 | 17 | 0 | 8 | | 0 | 0 | 0 | 0 | 0.18 |
| [D] 4.1% Cu, 3.7% Fe/SiO₂ | 281 | 52 | 10 | 8 | 15 | 1 | 5 | 3 | 6 | 1 | 7.2 |
| [E] 0.45% K, 1.3% Ru | 244 | 60 | 1 | 11 | 7 | 3 | 2 | 5 | 7 | 4 | 10.1 |
| [F] 0.3% K, 1.4% ir | 250 | 76 | 17 | 7 | 0 | 0 | 0 | 0 | 0 | 0 | 0.23 |

[a] Bimetallic cluster catalysts prepared by the method of the instant invention. H₂/CO = 3.0, 103 kPA total pressure, 0.4 gm catalyst.

What is claimed is:

1. In a Fischer-Tropsch process reaction for the production of hydrocarbons from CO and H₂ wherein CO and H₂ are passed over a catalyst the improvement comprising using as the catalyst a supported potassium or rubidium-Group VIII metal cluster catalyst which catalyst is prepared by depositing a known, well-characterized potassium or rubidium-Group VIII metal carbonyl cluster complex on a high surface area support, drying the carbonyl cluster complex impregnated support in the absence of oxygen and reducing the supported complex at elevated temperatures, wherein using this catalyst in Fischer-Tropsch processes results in the selective formation of higher molecular weight paraffinic and olefinic hydrocarbons.

2. The process of claim 1 wherein the catalyst comprises a supported, potassium-Group VIII metal cluster catalyst.

3. The process of claim 1 wherein the catalyst comprises a supported rubidium-Group VIII metal cluster catalyst.

4. The process of claim 1 wherein the Group VIII metal is selected from the group consisting of ruthenium, cobalt, rhodium, iridium, nickel, palladium, platinum and iron.

5. The process of claim 4 wherein the Group VIII metal is selected from the group consisting of iron, ruthenium and iridium.

6. The process of claim 1 wherein the support is selected from the group consisting of refractory inorganic oxides and carbon.

7. The process of claim 6 wherein the refractory inorganic oxides are selected from the group consisting of alumina, silica, silica-alumina, titania, zirconia, hafnia, tantala, niobium, vanadium, tungsten oxide, magnesia, chromia and molybdenum.

8. The process of claim 7 wherein the refractory inorganic oxides are selected from the group consisting of alumina, silica-alumina, titania, magnesia, hafnia and zirconia.

9. The process of claim 1 wherein the supported potassium or rubidium-Group VIII metal carbonyl cluster complex is reduced at a temperature of from 200° to 800° C.

10. The process of claim 9 wherein the reduction temperature ranges from 350° to 600° C.

11. The process of claim 10 wherein the reduction temperature ranges from 400° to 500° C.

12. The process of claim 1 wherein the Group VIII-metal constitutes 0.1 to 50% by weight of the catalyst.

13. The process of claim 1 wherein the Group VIII metal to potassium or rubidium mole ratio ranges from between 0.33 to 20.

14. The process of claim 2 wherein the Group VIII metal is iron.

15. The process of claim 14 wherein the potassium to iron mole ratio is 2 and the support is alumina.

* * * * *